US008236425B2

(12) United States Patent
Moore et al.

(10) Patent No.: US 8,236,425 B2
(45) Date of Patent: *Aug. 7, 2012

(54) LONG-CHAIN POLYMETHYLENE HALIDE TELOMERS

(75) Inventors: George G. I. Moore, Afton, MN (US); Yu Yang, Eden Prairie, MN (US); Richard M. Flynn, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 407 days.

This patent is subject to a terminal disclaimer.

(21) Appl. No.: 12/519,573

(22) PCT Filed: Dec. 27, 2007

(86) PCT No.: PCT/US2007/088903
§ 371 (c)(1),
(2), (4) Date: Jun. 17, 2009

(87) PCT Pub. No.: WO2008/083199
PCT Pub. Date: Jul. 10, 2008

(65) Prior Publication Data
US 2010/0093925 A1    Apr. 15, 2010

Related U.S. Application Data

(60) Provisional application No. 60/882,798, filed on Dec. 29, 2006, provisional application No. 60/882,810, filed on Dec. 29, 2006.

(51) Int. Cl.
*B32B 27/00* (2006.01)

(52) U.S. Cl. ........ 428/421; 526/242; 526/243; 526/244; 526/245; 526/248; 526/255; 427/427.4; 427/430.1; 570/125; 570/139; 570/171; 560/205; 524/544

(58) Field of Classification Search .......... 526/245; 570/125, 139, 171; 524/544
See application file for complete search history.

(56) References Cited

U.S. PATENT DOCUMENTS

| | | | |
|---|---|---|---|
| 2,440,800 A | 5/1948 | Hanford et al. | |
| 2,440,801 A | 5/1948 | Hanford et al. | |
| 2,457,229 A | 12/1948 | Hanford et al. | |
| 2,567,011 A | 1/1949 | Diesslin et al. | |
| 2,519,983 A | 8/1950 | Simons | |
| 2,592,069 A | 4/1952 | Reid | |
| 2,642,416 A | 6/1953 | Ahlbrecht et al. | |
| 2,662,835 A | 12/1953 | Reid | |
| 2,693,458 A | 11/1954 | Olson | |
| 2,727,923 A | 12/1955 | Husted | |
| 2,732,398 A | 1/1956 | Brice et al. | |
| 2,759,019 A | 8/1956 | Brown et al. | |
| 2,764,602 A | 9/1956 | Ahlbrecht | |
| 2,764,603 A | 9/1956 | Ahlbrecht | |
| 2,803,615 A | 8/1957 | Albrecht et al. | |
| 2,803,656 A | 8/1957 | Ahlbrecht et al. | |
| 2,809,990 A | 10/1957 | Brown et al. | |
| 2,846,472 A | 8/1958 | Van Dyke Tiers | |
| 2,875,253 A | 2/1959 | Barnhart | |
| 2,915,554 A | 12/1959 | Ahlbrecht et al. | |
| 3,016,407 A | 1/1962 | Brace | |
| 3,050,555 A | 8/1962 | Van Dyke Tiers | |
| 3,055,953 A * | 9/1962 | Smeltz ..................... 570/125 |
| 3,068,187 A | 12/1962 | Archibald et al. | |
| 3,094,547 A | 6/1963 | Heine | |
| 3,102,103 A | 8/1963 | Ahlbrecht et al. | |
| 3,145,222 A | 8/1964 | Brace | |
| 3,171,861 A | 3/1965 | Ahlbrecht | |
| 3,341,497 A | 9/1967 | Sherman et al. | |
| 3,398,182 A | 8/1968 | Guenthner et al. | |
| 3,514,487 A | 5/1970 | Anello et al. | |
| 3,562,156 A | 2/1971 | Francen | |
| 3,573,332 A | 3/1971 | Fenton | |
| 3,574,791 A | 4/1971 | Sherman et al. | |
| 3,592,866 A | 7/1971 | Magoon et al. | |
| 3,641,171 A | 2/1972 | Spooncer | |
| 3,787,351 A | 1/1974 | Olson | |
| 3,818,074 A | 6/1974 | Ahlbrecht | |
| 3,842,019 A | 10/1974 | Kropp | |
| 3,896,251 A | 7/1975 | Landucci | |
| 3,916,053 A | 10/1975 | Sherman et al. | |
| 4,024,178 A | 5/1977 | Landucci | |
| 4,043,923 A | 8/1977 | Loudas | |

(Continued)

FOREIGN PATENT DOCUMENTS

| | | |
|---|---|---|
| EP | 0 526 976 B1 | 1/1997 |
| GB | 1102903 | 2/1968 |
| GB | 1 415 245 | 11/1975 |
| WO | WO 2008/027736 | 3/2008 |
| WO | WO 2008/083201 | 7/2008 |

OTHER PUBLICATIONS

*Encyclopedia of Polymer Science and Engineering*, "Telomerization", John Wiley & Sons, Inc., vol. 16, pp. 533-554 (1989).

Boyer et al., "Reverse Iodine Transfer Polymerization (RITP) of Methyl Methacrylate", *Macromolecules*, pp. 4044-4053, vol. 39 (2006).

(Continued)

*Primary Examiner* — Mark Eashoo
*Assistant Examiner* — Nicole M Buie-Hatcher
(74) *Attorney, Agent, or Firm* — Lucy C. Weiss

(57) ABSTRACT

A composition comprises a distribution of telomers of ethylene and at least one fluoroalkyl or perfluoroalkyl halide, the telomers comprising at least one polymethylene segment ($-(CH_2)_n-$) and at least one halomethyl group ($-CXH_2$) and optionally comprising at least one non-fluorine heteroatom, and the halogen being selected from iodine and bromine; wherein the distribution has a number average ratio of methylene moieties of the polymethylene segment to the halomethyl groups of at least about 15.

20 Claims, No Drawings

U.S. PATENT DOCUMENTS

| | | | |
|---|---|---|---|
| 4,058,573 A * | 11/1977 | Knell | 570/172 |
| 4,147,851 A | 4/1979 | Raynolds | |
| 4,264,484 A | 4/1981 | Patel | |
| 4,359,096 A | 11/1982 | Berger | |
| 4,401,780 A | 8/1983 | Steel | |
| 4,484,990 A | 11/1984 | Bultman et al. | |
| 4,529,658 A | 7/1985 | Schwartz et al. | |
| 4,540,497 A | 9/1985 | Chang et al. | |
| 4,564,561 A | 1/1986 | Lore et al. | |
| 4,606,737 A | 8/1986 | Stern | |
| 4,668,406 A | 5/1987 | Chang | |
| 4,716,208 A | 12/1987 | Korzeniowski | |
| 5,025,052 A | 6/1991 | Crater et al. | |
| 5,207,996 A | 5/1993 | Sierakowski et al. | |
| 5,216,097 A | 6/1993 | Allewaert et al. | |
| 5,240,574 A | 8/1993 | Fub et al. | |
| 5,244,951 A | 9/1993 | Gardiner | |
| 5,271,806 A | 12/1993 | Deutsch et al. | |
| 5,276,175 A | 1/1994 | Dams et al. | |
| 5,380,778 A | 1/1995 | Buckanin | |
| 5,431,833 A | 7/1995 | Kondo et al. | |
| 5,451,622 A | 9/1995 | Boardman et al. | |
| 5,459,212 A * | 10/1995 | Krespan et al. | 526/89 |
| 5,468,353 A | 11/1995 | Anich et al. | |
| 5,612,431 A | 3/1997 | Waddell et al. | |
| 5,641,844 A | 6/1997 | Thompson et al. | |
| 5,725,789 A | 3/1998 | Huber et al. | |
| 5,744,201 A | 4/1998 | Chang et al. | |
| 6,048,952 A | 4/2000 | Behr et al. | |
| 6,326,447 B1 | 12/2001 | Fitzgerald | |
| 6,365,769 B1 | 4/2002 | Behr et al. | |
| 6,824,882 B2 | 11/2004 | Boardman et al. | |
| 2005/0119430 A1 | 6/2005 | Jong et al. | |
| 2010/0234521 A1 * | 9/2010 | Flynn et al. | 524/544 |

OTHER PUBLICATIONS

Boyer et al., "Iodine Transfer Polymerization (ITP) of Vinylidene Fluoride (VDF). Influence of the Defect of VDF Chaining on the Control of ITP", *Macromolecules*, pp. 10353-10362, vol. 38 (2005).

Brace, "Radical Addition of Iodoperfluoroalkanes to Vinyl and Allyl Monomers", Contribution No. 313, Research Division, Organic Chemicals Department, E.I. du Pont de Nemours and Company, Wilmington, Delaware, *Journal of Organic Chemistry*, pp. 3033-3038, vol. 27 (Sep. 1962).

International Search Report for International Application No. PCT/US2007/088903.

* cited by examiner

LONG-CHAIN POLYMETHYLENE HALIDE TELOMERS

STATEMENT OF PRIORITY

This application claims the priority of U.S. Provisional Application Nos. 60/882,798 and 60/882,810 filed Dec. 29, 2006, the contents of which are hereby incorporated by reference.

FIELD

This invention relates to telomers of ethylene and fluoroalkyl or perfluoroalkyl halides.

BACKGROUND

Fluorinated polymers typically comprise repeating units, each unit including a backbone portion attached to a fluoroalkyl side chain. The fluoroalkyl side chain typically includes a hydrocarbon spacer group and a terminal perfluoroalkyl tail. The stable and inert perfluoroalkyl tail is hydrophobic and oleophobic.

Such fluorinated polymers can be mixed with an inert carrier or dissolved in a solvent and applied to a hydrophilic material (for example, paper, cloth, metals, glass, or ceramic) to impart water and oil repellency to the material. The perfluoroalkyl tail portions of the polymer can organize or align at the solid/air interface of the material to create a low energy surface.

Conventional fluoroalkyl side chains generally have the formula $C_nF_{2n+1}(CH_2)_m$— where n typically ranges from 6 to 12, and m typically ranges from 1 to 11. Adjustment of the number of methylene moieties (—$CH_2$—) in the spacer group, as well as the number of carbon atoms in the $C_nF_{2n+1}$ perfluoroalkyl tail, can result in the organization or alignment of the side chains of the polymers and in the formation of crystalline-like regions when the polymer is applied to a substrate material. It has been postulated that an increase in the number of methylene moieties in the spacer group can compensate for the decrease in the value of n that is now viewed as desirable from an environmental residue perspective.

In synthesizing conventional fluorinated polymers, however, the perfluoroalkyl chain length generally has been the only part of the side chain that has been varied to enhance the formation of crystalline regions (and the accompanying ability to impart low surface energy characteristics). This may have been due to a scarcity of industrially useful methods for preparing side chains of varying polymethylene content.

Compounds comprising polymethylene moieties have been prepared by different synthetic techniques, but each has its own advantages and disadvantages. One such method has been the telomerization of ethylene using various telogens.

Telomerization has been defined as the process of reacting, under polymerization conditions, a molecule YZ (termed a "telogen") with more than one unit of a polymerizable compound having ethylenic unsaturation (termed a "taxogen") to form products called "telomers" having the formula $Y(A)_nZ$, wherein $(A)_n$ is a divalent radical formed by chemical union, with the formation of new carbon bonds, of n molecules of the taxogen (the unit A being termed a "taxomon," n being any integer greater than one, and Y and Z being fragments of the telogen attached to the terminal taxomons). Telomerization is distinct from interpolymerization (more commonly referred to as copolymerization), in that in telomerization only one molecule of telogen is incorporated into each resulting telomer molecule, and the average molecular weight of the telomer product is, in general, considerably lower than that of an interpolymer formed under comparable conditions.

Ethylene telomerization produces a mixture or distribution of telomers having varying numbers of methylene moieties. For the telogens selected and the conditions utilized, however, ethylene telomerizations have typically resulted in telomers of only limited chain length. Industrial use of fluoroalkyl or perfluoroalkyl halides, in particular, has typically focused on the incorporation of only one molecule of ethylene (n=1).

SUMMARY

Thus, we recognize that there is a need for sidechain precursor compounds having varying numbers of methylene moieties (and processes for their preparation). In particular, there is a need for sidechain precursor compounds having more than the 1-11 methylene moieties found in sidechains made by conventional synthetic techniques (for repellency applications, preferably, in combination with a terminal fluorinated group).

Briefly, in one aspect, this invention provides such a composition, which comprises a distribution of telomers of ethylene and at least one fluoroalkyl or perfluoroalkyl halide, the telomers comprising at least one polymethylene segment (—$(CH_2)_n$—) and at least one halomethyl group (—$CXH_2$) and optionally comprising at least one non-fluorine heteroatom, and the halogen being selected from iodine and bromine; wherein the distribution has a number average ratio of methylene moieties of the polymethylene segment to halomethyl groups of at least about 15. Preferably, the number average ratio is at least about 20.

As used herein, the term "number average ratio" means the average ratio that is calculated from the number average molecular weight of the telomer distribution. The number average molecular weight of the telomer distribution can be determined by nuclear magnetic resonance spectroscopy (NMR), gas chromatography (GC), or other suitable techniques (preferably, by NMR).

It has been discovered that fluoroalkyl halide and perfluoroalkyl halide telogens can be used to produce long-chain telomers of ethylene. The telomers can contain more than 10 methylene moieties and, for example, up to as many as 30 methylene moieties or more (for example, up to as many as 50), depending upon, for example, the selected reactants, ratios of reactants, and reaction conditions. The telomers can be produced in the form of a distribution (that is, a mixture of varying chain-length compounds, which differ in the number of incorporated ethylene units), and, unlike conventional polymethylene telomer distributions that have a number average ratio of internal methylene moieties (for example, of the ethylene taxomons derived from the ethylene taxogen) to terminal halomethyl groups (for example, comprising the halogen atom of the selected telogen) of no more than about 7, the distributions can exhibit number average ratios of at least about 15 (preferably, at least about 20).

At least some embodiments of the telomer distribution can be used as fluoroalkyl sidechain precursors and, for many applications, can meet the need for sidechain precursor compounds having more than the 1-11 methylene moieties found in conventional sidechains. Such embodiments provide an economical source of crystallizable polymethylene, as they can be prepared, for example, without the need for multiple reaction steps. In addition, the telomers of such embodiments can comprise a relatively short perfluoroalkyl tail portion that can be lower in cost (and easier to prepare and process) than longer perfluoroalkyl tail portions and that is also believed to provide for relatively low bio-accumulation. Such embodiments therefore can be environmentally friendly, yet still can be effective in imparting fluorochemical repellency characteristics (for example, water and oil repellency), apparently due to the above-mentioned compensation effect of the lengthy polymethylene segment (which enables the use of the shorter perfluoroalkyl tail portion).

The fluoroalkyl halide telomer distribution of the invention can be converted to a distribution of telomer derivatives, in which the halogen (iodine or bromine) of the telomers is replaced with an organic functional moiety, Z, that is selected from carbonyl-containing, sulfur-containing, alkenyl-containing, nitrogen-containing, and oxygen-containing moieties, and combinations thereof. Preferably, Z is selected from hydroxyl, amino, carboxyl, mercapto, sulfonato, and vinyl moieties, and combinations thereof. The derivatives can be useful, for example, as surfactants, as catalysts, and in protective coatings.

The hydroxyl-containing derivatives, for example, can be further converted to acrylates, methacrylates, or urethanes (or a combination thereof), which can be used to prepare fluoropolymers for use, for example, in coating compositions for imparting repellency (for example, oil and water repellency) to various substrates. Thus, the invention further provides a fluoropolymer prepared from the acrylate, methacrylate, or urethane (or a combination thereof) derivatives of the composition of the invention; a coating composition comprising the fluoropolymer and a liquid carrier; a process comprising applying the coating composition to at least a portion of at least one surface of at least one substrate; and a coated article comprising at least one substrate bearing the coating composition or the fluoropolymer component of the coating composition on at least a portion of at least one surface thereof.

DETAILED DESCRIPTION

Definitions

As used in this patent application:

"catenated heteroatom" means an atom other than carbon (for example, oxygen, nitrogen, silicon, or sulfur) that is bonded to carbon atoms in a carbon chain so as to form a carbon-heteroatom-carbon chain;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Telogens

Telogens that can be suitable for use in preparing the composition of the invention include fluoroalkyl halide and perfluoroalkyl halide compounds that optionally contain one or more non-fluorine heteroatoms. The halides can be iodides or bromides or a mixture thereof. Iodides can be preferred due to the availability of a wide variety of iodide compounds, and bromides, although previously viewed as less reactive and therefore less available, can be preferred due to their lower cost. Preferably, the optional heteroatoms are selected from iodine, bromine, nitrogen, oxygen, and sulfur. More preferably, the heteroatoms are present as a single iodine or bromine atom, as a catenated oxygen, nitrogen, or sulfur atom (for example, an ether oxygen moiety, the in-chain oxygen atom of an ester moiety, or the in-chain sulfur atom of a sulfonyl moiety), or as part of a terminal functional group (for example, carboxyl, cyano, sulfonato, acyloxy (or alkyl carboxylate), sulfonamido, and carboxamido moieties, and the like, and combinations thereof). The fluoroalkyl and perfluoroalkyl groups can optionally comprise one or more cyclic moieties. Preferably, the telogens are saturated.

One class of suitable telogens is that which can be represented by the following general formula:

$$RC(R)(R)X \qquad (I)$$

wherein each R is independently hydrogen, fluorine, or an alkyl, fluoroalkyl, or perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one non-fluorine heteroatom and/or at least one alicyclic moiety, with the proviso that two R groups can be bonded together to form an alicyclic ring having 5 to about 7 ring carbon atoms, and with the further proviso that at least one of the R groups comprises fluorine; and X is iodine or bromine. Preferably, the optional heteroatom is selected from iodine, bromine, nitrogen, oxygen, and sulfur (more preferably, nitrogen, oxygen, and sulfur; even more preferably, nitrogen or oxygen; most preferably, oxygen).

Preferably, at least one R group is hydrogen or fluorine. More preferably, one R group is hydrogen or fluorine; one R group is hydrogen, fluorine, or perfluoroalkyl; and one R group is an alkyl, fluoroalkyl, or perfluoroalkyl group that optionally comprises at least one non-fluorine heteroatom. Even more preferably, one R group is hydrogen or fluorine; one R group is hydrogen, fluorine, perfluoroisopropyl, or perfluoromethyl (more preferably, hydrogen, fluorine, or perfluoromethyl); and one R group is a fluoroalkyl or perfluoroalkyl group that optionally comprises at least one non-fluorine heteroatom. Most preferably, two R groups are hydrogen or fluorine (preferably, both are hydrogen or both are fluorine) or one R group is hydrogen or fluorine and another R group is perfluoromethyl; and one R group is a fluoroalkyl or perfluoroalkyl group that optionally comprises at least one non-halogen heteroatom. The telogen preferably is saturated and preferably does not comprise an alicyclic moiety.

Preferred telogens for use in preparing the composition of the invention include fluoroalkyl halides that comprise at least one halomethylene moiety (—CHX—) and, optionally, at least one non-fluorine heteroatom; perfluoroalkyl halides that comprise at least one halofluoromethylene moiety (—CFX—) and at least one non-halogen heteroatom; and mixtures thereof.

One class of suitable fluoroalkyl halides is that which can be represented by the following general formula:

$$R''CH(R')X \qquad (II)$$

wherein R" is fluorine or a fluoroalkyl or perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one non-fluorine heteroatom and/or at least one alicyclic moiety; R' is hydrogen, fluorine, or a fluoroalkyl or perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one non-fluorine heteroatom and/or at least one alicyclic moiety; and X is iodine or bromine; with the proviso that R'' and R' can be bonded together to form an alicyclic ring having from 5 to about 7 ring carbon atoms. Preferably, the heteroatom is selected from iodine, bromine, nitrogen, oxygen, and sulfur (more preferably, nitrogen, oxygen, and sulfur; even more preferably, nitrogen or oxygen; most preferably, oxygen).

R'' is preferably a fluoroalkyl or perfluoroalkyl group that optionally comprises at least one non-fluorine heteroatom. R' is preferably hydrogen or perfluoroalkyl (more preferably, hydrogen, perfluoroisopropyl, or perfluoromethyl; most preferably, hydrogen or perfluoromethyl). R'' and R' preferably do not comprise an alicyclic moiety.

Representative examples of suitable fluoroalkyl halide telogens include $CF_3CH_2I$, $CF_3OCH(CF_3)I$, $CF_3CH(CF_3)Br$, $H(CF_2)_6CH_2I$, $CF_3C_3H_6I$, $C_2F_5C_2H_4I$, $CF_3CH_2Br$, $C_2F_5C_2H_4Br$, $(CF_3)_2CFCH_2I$, $C_4F_9C_2H_4I$, $C_4F_9C_4H_8I$, $C_4F_9C_4H_8Br$, $C_6F_{13}CH_2Br$, $CF_3OC_2H_4I$, $C_4F_9OCH_2Br$, $C_3F_7CH_2OC_2H_4I$, $C_4F_9SO_2N(CH_3)C_2H_4I$, $C_2F_5OC_2F_4C_2H_4I$, $CF_3OC_2F_4CH_2Br$, $(CF_3)_2CHOC_2H_4I$, $C_2F_5SO_2N(CH_3)CH_2C(O)CH_2I$, $(CF_3)_2NC_2F_4CH_2I$, $C_3F_7N(CF_3)CF_2C_2H_4Br$, $FSO_2C_3F_6C_2H_4I$, $(CF_3)_2NCH_2I$, $(CF_3)_2NCF_2CH_2I$, $CH_3OC(O)C_4F_8CH_2I$, $CH_3OC(O)C_2F_4I$, $(CF_3)_2CHI$, and the like, and mixtures thereof. Also useful are telogen mixtures (for example, $C_4F_9(CH_2)_nI$, where n is a number average value (that is, an average value that is calculated from the number average molecular weight of the mixture) of 1 to about 17) that can be obtained, for example, as a distribution from a prior, "partial" telomerization and recycled for further telomerization.

Preferred fluoroalkyl halide telogens include $CH_3OC(O)C_4F_8CH_2I$, $C_2F_5C_2H_4I$, $(CF_3)_2CFCH_2I$, $C_4F_9C_2H_4I$, $C_2F_5SO_2N(CH_3)CH_2C(O)CH_2I$, $C_4F_9SO_2N(CH_3)C_2H_4I$, $CF_3OC_2F_4CH_2Br$, $(CF_3)_2CHOC_2H_4I$, $CH_3OC(O)C_2F_4I$, $(CF_3)_2CHI$, and mixtures thereof. More preferred are $(CF_3)_2CFCH_2I$, $C_4F_9C_2H_4I$, $C_4F_9SO_2N(CH_3)C_2H_4I$, $CF_3OC_2F_4CH_2Br$, $(CF_3)_2CH(O)C_2H_4I$, $(CF_3)_2CHI$, and mixtures thereof, with $(CF_3)_2CFCH_2I$, $C_4F_9C_2H_4I$, $C_4F_9SO_2N(CH_3)C_2H_4I$, $CH_3OC(O)C_2F_4I$, $(CF_3)_2CHI$, and mixtures thereof being most preferred.

One class of suitable perfluoroalkyl halides is that which can be represented by the following general formula:

$$R''''CF(R''')X \qquad (III)$$

wherein R'''' is a perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one alicyclic moiety and/or at least one non-fluorine halogen atom (preferably, iodine or bromine; when present, preferably only one such halogen atom); R''' is fluorine or a perfluoroalkyl group of 1 to about 25 carbon atoms (preferably, 1 to about 10 carbon atoms; more preferably, 1 to about 6 carbon atoms; most preferably, 1 to about 4 carbon atoms); and X is iodine or bromine; with the proviso that at least one of R'''' and R''' comprises at least one non-halogen heteroatom, and with the further proviso that R'''' and R''' can be bonded together to form an alicyclic ring having from 5 to about 7 ring carbon atoms. Preferably, the heteroatom is selected from nitrogen, oxygen, and sulfur (more preferably, nitrogen or oxygen; most preferably, oxygen).

R'''' preferably is a perfluoroalkyl group that comprises at least one non-halogen heteroatom. R''' is preferably fluorine or perfluoroalkyl (more preferably, fluorine, perfluoroisopropyl, or perfluoromethyl; most preferably, fluorine or perfluoromethyl). R'''' and R''' preferably do not comprise an alicyclic moiety or a non-fluorine halogen atom.

Representative examples of suitable perfluoroalkyl halide telogens include $C_4F_9I$, $C_5F_{11}Br$, $C_6F_{13}I$, $FSO_2C_2F_4OC_2F_4I$, $FSO_2C_3F_6Br$, $CF_3OC_2F_4I$, $CF_3OCF(CF_3)I$, $(CF_3)_2CFOC_2F_4I$, $C_3F_7O(i-C_3F_6O)_pCF(CF_3)I$ (where p is an integer of 0 to 7), $C_3F_7O(n-C_3F_6O)_pCF(CF_3)I$ (where p is an integer of 0 to 7), $C_3F_7O(i-C_3F_6O)_pCF(CF_3)Br$ (where p is an integer of 0 to 7), $FOC(O)C_5F_{10}I$, and the like, and mixtures thereof. Preferred perfluoroalkyl halide telogens include $C_4F_9I$, $C_5F_{11}Br$, $C_6F_{13}I$, $FSO_2C_2F_4OC_2F_4I$, $FSO_2C_3F_6Br$, $CF_3OC_2F_4I$, $FOC(O)C_5F_{10}I$, $(CF_3)_2CFOC_2F_4I$, $C_3F_7O(i-C_3F_6O)_pCF(CF_3)I$ (where p is an integer of 5 to 7), and mixtures thereof. More preferred are $C_4F_9I$, $C_5F_{11}Br$, $C_6F_{13}I$, $FSO_2C_2F_4OC_2F_4I$, $FOC(O)C_5F_{10}I$, $(CF_3)_2CFOC_2F_4I$, $C_3F_7O(i-C_3F_6O)_pCF(CF_3)I$ (where p is an integer of 5 to 7), and mixtures thereof, with $C_4F_9I$, $FSO_2C_2F_4OC_2F_4I$ and $C_3F_7O(i-C_3F_6O)_pCF(CF_3)I$ (where p is an integer of 5 to 7), and mixtures thereof being most preferred.

Preferred telogens include those that comprise a sulfonamido moiety, a perfluoropolyether moiety, or a relatively low carbon number (fewer than about 6 carbon atoms) perfluoroalkyl moiety, as such telogens tend to provide telomer distributions that can exhibit relatively low bio-accumulation characteristics. In general, preferences can be based upon economic factors (for example, cost, availability, or ease of handling) or upon performance factors (for example, of the telogen or the resulting telomer distribution).

The heteroatoms can be present in the fluoroalkyl halide and perfluoroalkyl halide telogens in the form of functional groups (for example, alkoxy, alkanoyloxy, alkyloxyacyl, cyano, sulfonyl, and like groups having no active hydrogen atoms). Such functional groups can be useful as strong acids for catalysts (for example, —COOH or —SO$_3$H) or anionic surfactants or as reactive intermediates (for example, as in polymer formation). The additional non-fluorine halogen atoms, when in the form of iodine or bromine bonded to carbon, can provide additional reactive sites for insertion of ethylene. Preferred telogens include the fluoroalkyl halides and mixtures thereof.

The above-described telogens can be prepared by known methods. For example, the fluoroalkyl halides can be prepared by displacement of a leaving group (on the fluoroalkyl moiety) by bromide or iodide, and the perfluoroalkyl halides can be prepared by the reaction of a perfluoroolefin (for example, tetrafluoroethylene or hexafluoropropylene) with IF$_5$ or by decarbonylation of perfluoroacyl halides. Some of the telogens (for example, $FSO_2C_2F_4OC_2F_4I$ and $I(CF_2)_4I$) are commercially available.

Telomer Preparation

The process of preparing the telomer composition of the invention can be conducted neat or, optionally, in the presence of a reaction diluent that is liquid at the selected reaction temperature and pressure, that is capable of dissolving or dispersing the reactants and initiator(s), and that is inert to the reactants, the initiator(s), and the resulting telomer products. Suitable diluents include water (for suspension or emulsion techniques), supercritical carbon dioxide, perfluorocarbons, hydrofluoroethers (HFEs), hexafluorobenzene, trifluorotoluene, hexafluoroxylene, alkanes, benzene, and the like, and mixtures thereof). Preferred diluents include fluorine-containing diluents, due to their generally low reactivity toward free radical intermediates. If desired, a portion of the telomer product can serve as at least a portion of the diluent (with less or no added diluent being required). Amounts of diluent up to about 30 times the weight of telogen generally can be employed.

The telomerization process can be conducted by any of a variety of procedures. If desired, ethylene, telogen(s), free radical initiator(s), and diluent(s) can be charged (in essentially any order and manner of combination) to an autoclave or similar pressure reactor (made, for example, of stainless steel, optionally with a glass liner, and optionally equipped with agitation means). The process can be carried out in a batchwise manner. Alternatively, the process can be carried out in a semi-continuous or continuous manner (with continuous introduction of reactants and/or continuous removal of product) by, for example, using a tubular reactor. If desired, one reaction component can be added to the other reaction components in increments (for example, by adding ethylene to a solution of telogen and free radical initiator). The various different manners of carrying out the process can be combined, if desired.

The telomerization process can be preferably and most efficiently conducted at elevated temperature and pressure. In general, temperatures varying from about 0° C. to about 250° C. can be utilized (depending, for example, upon the particular free radical initiator that is selected), with temperatures from about 75° C. to about 125° C. often being preferred. In general, a preferred temperature can reflect a selected balance between lower reactivity at lower temperatures and an increased tendency toward side reactions at higher temperatures.

Reaction pressures from about 10 atmospheres to about 350 atmospheres (preferably, from about 50 atmospheres to about 350 atmospheres; more preferably, from about 100 atmospheres to about 350 atmospheres) generally can be satisfactory. If desired, the telomerization process can be conducted in an inert reaction environment, so that the presence of reactive materials such as oxygen can be avoided. Preferably, the reaction conditions can be substantially oxygen-free.

In general, molar ratios of the total amount of ethylene to the total amount of telogen ("total molar ratios") of from about 4:1 to about 400:1 can be satisfactory, with total molar ratios from about 8:1 to about 300:1 being preferred (more preferably, about 10:1 to about 200:1; even more preferably, about 50:1 to about 150:1; most preferably, about 70:1 to about 125:1). The selection of total molar ratio will depend upon the desired methylene moiety content of the telomer product relative to the methylene moiety content of the starting telogen and will generally be at least about twice the number of moles of ethylene desired to be incorporated through the telomerization process per mole of telogen. (In general, at lower ratios, the rate and degree of telomerization can be lower than desired.)

Although such total (or overall) molar ratios generally can be maintained throughout the process, some deviation (for example, for less than about 25 percent of the total reaction time) can be tolerated and is to be expected as ethylene is consumed. The instantaneous molar ratio of ethylene to telogen thus can vary over a wide range, although it generally can be useful to employ a stoichiometric excess of ethylene (relative to the desired telomer product).

Free radical-generating initiators are well-known. Useful thermal free radical initiators include, but are not limited to, the following: (1) azo compounds such as, for example, 2,2'-azo-bis(isobutyronitrile), 2,2'-azo-bis(isovaleronitrile), dimethyl 2,2'-azo-bis(isobutyrate), azo-bis(diphenyl methane), and 4,4'-azo-bis(4-cyanopentanoic acid); (2) peroxides such as, for example, hydrogen peroxide, benzoyl peroxide, cumyl peroxide, tert-butyl peroxide, cyclohexanone peroxide, glutaric acid peroxide, lauroyl peroxide, and methyl ethyl ketone peroxide; (3) hydroperoxides such as, for example, tert-butyl hydroperoxide and cumene hydroperoxide; (4) peracids such as, for example, peracetic acid, perbenzoic acid, potassium persulfate, and ammonium persulfate; (5) peresters such as, for example, tert-butyl perbenzoate and diisopropyl percarbonate; (6) thermal redox initiators; and the like; and mixtures thereof.

Preferred free radical initiators include azo compounds, peroxides, peresters, and mixtures thereof. More preferred are free radical initiators selected from 2,2'-azo-bis(isobutyronitrile), 2,2'-azo-bis(isovaleronitrile), benzoyl peroxide, tert-butyl peroxide, tert-butyl perbenzoate, and mixtures thereof (most preferably, those selected from 2,2'-azo-bis(isobutyronitrile), tert-butyl perbenzoate, and mixtures thereof). The free radical initiator can be used in a catalytically effective amount (for example, up to about 5 weight percent (preferably, about 1 to about 5 weight percent; more preferably, about 2 weight percent), based upon the total weight of telogen). Initiator can be added all at once or in increments, as desired.

The telomer product distribution from the reactor can be used as recovered or, optionally, can be separated into a telomer fraction having a higher selected numerical range of carbon atoms and a telomer fraction having a lower selected numerical range of carbon atoms by using, for example, fractional distillation, selective extraction, adsorption, and the like, and combinations thereof. The lower telomer fraction, along with any unreacted telogen, can be recycled to the reactor for further reaction with ethylene to produce additional higher molecular weight (longer chain) telomer products. Generally, however, relatively long-chain telomers can be produced (by proper selection of the ratio of reactants and the reaction temperature) without the need for such separation and recycling.

Product Composition

The resulting composition comprises a distribution of fluoroalkyl halide telomers that comprise at least one polymethylene segment ($-(CH_2)_n-$) and at least one halomethyl group ($-CXH_2$). The telomers optionally comprise at least one non-fluorine heteroatom, and the halogen is selected from iodine and bromine. The distribution exhibits a number average ratio (that is, an average ratio calculated from the number average molecular weight of the distribution) of the methylene moieties of the polymethylene segment to the halomethyl groups of at least about 15. The number average molecular weight of the distribution can be determined by nuclear magnetic resonance spectroscopy (NMR), gas chromatography (GC), or other suitable techniques (preferably, by NMR). Preferably, the number average ratio of the distribution is at least about 20 (in view of, for example, preferred crystallization characteristics).

One class of product telomer distributions is that which can be represented by the following general formula:

$$RCR(R)-(CH_2)_n-X \qquad (IV)$$

wherein R and X are as defined above for Formula I, and n is a number average value (that is, an average value calculated from the number average molecular weight of the distribution) of at least about 15 (preferably, at least about 20).

A preferred class of product telomer distributions is that which can be represented by the following general formula:

$$R''CH(R')-(CH_2)_n-X \qquad (V)$$

wherein R'', R', and X are as defined above for Formula II, and n is a number average value of at least about 15 (preferably, at least about 20).

Another preferred class of product telomer distributions is that which can be represented by the following general formula:

$$R''''CF(R''')-(CH_2)_n-X \qquad (VI)$$

wherein R'''', R''', and X are as defined above for Formula III, and n is a number average value of at least about 15 (preferably, at least about 20).

Representative examples of such telomer distributions include $C_4F_9(CH_2)_nI$, $C_5F_{11}(CH_2)_nBr$, $C_6F_{13}(CH_2)_nI$, $CF_3(CH_2)_nI$, $CF_3CF_2(CH_2)_nI$, $(CF_3)_2NCF_2(CH_2)_nI$, $CF_3C_2F_4(CH_2)_nI$, $C_3F_7O(C_3F_6O)_5CF(CF)(CH_2)_nI$, $C_4F_9SO_2N(CH_3)(CH_2)_nI$, $FSO_2C_2F_4OC_2F_4(CH_2)_nI$, $CH_3OC(O)CF_2(CH_2)_nI$, $FOC(O)CF_2(CH_2)_nI$, $(CF_3)_2CF(CH_2)_nI$, $(CF_3)_2N(CH_2)_nI$, $(CF_3)_2CHO(CH_2)_nI$, $SF_5CF_2(CH_2)_nI$, $CF_3OC_2F_4(CH_2)_nBr$, $(CF_3)_2CH(CH_2)_nI$, $(CF_3)_3C(CH_2)_nBr$, $C_4F_9SO_2N(CH_3)CH_2C(O)(CH_2)_nI$, where n is a number average value of at least about 15 (for example, 18, 20, 25, 26, 45, and the like), and the like, and mixtures thereof. Telomers having odd numbers of methylene moieties can be obtained by using telogens having an odd number of methylene moieties, which can be advantageous in varying the physical property characteristics (for example, melting point) of the resulting telomers.

Preferred telomer distributions include $C_4F_9(CH_2)_nI$, $C_5F_{11}(CH_2)_nBr$, $C_6F_{13}(CH_2)_nI$, $CF_3CF_2(CH_2)_nI$, $(CF_3)_2CH(CH_2)_nI$, $C_3F_7O(C_3F_6O)_5CF(CF_3)(CH_2)_nI$, $C_4F_9SO_2N(CH_3)(CH_2)_nI$, $(CF_3)_2CF(CH_2)_nI$, $CF_3OC_2F_4(CH_2)_nBr$, $CH_3OC(O)CF_2(CH_2)_nI$, $FSO_2C_2F_4OC_2F_4(CH_2)_nI$, $(CF_3)_2NCF_2(CH_2)_nI$, $(CF_3)_2CHO(CH_2)_nI$, where n is a number average value of at least about 15 (for example, 18, 20, 25, 26, and 45), and mixtures thereof, with $C_4F_9(CH_2)_nI$, $C_6F_{13}(CH_2)_nI$, $(CF_3)_2CH(CH_2)_nI$, $C_3F_7O(C_3F_6O)_5CF(CF_3)(CH_2)_nI$, $C_4F_9SO_2N(CH_3)(CH_2)_nI$, $(CF_3)_2CF(CH_2)_nI$, $CF_3OC_2F_4(CH_2)_nBr$, where n is a number average value of at least about 15 (for example, 18, 20, 25, 26, and 45), and mixtures thereof being more preferred.

The composition of the invention can comprise a mixture of such telomers that can be, for example, a relatively even or flat distribution of about 5 to about 10 different telomers, as indicated by gas chromatography.

Derivatives and Uses

The fluoroalkyl halide telomer compositions can be used, for example, as fluoroalkyl sidechain precursors in fluorinated polymer preparation. The compositions are reactive chemicals and can be converted into functional derivatives by one or more steps (for example, nucleophilic displacement or elimination reactions or free radical addition). Such functional derivatives can be useful in improving or imparting properties to solutions and substrates such as wetting, penetration, spreading, leveling, foaming, foam stabilization, flow properties, emulsification, dispersability, and oil, water, and soil repellency.

A class of such functional derivatives can be represented by modifications of Formulas IV-VI above, wherein X is replaced with an organic functional moiety, Z, which can contain one or more carbon atoms, and which can be selected from carbonyl-containing, sulfur-containing, alkenyl-containing, nitrogen-containing, and oxygen-containing moieties, and combinations thereof. Representative functional Z moieties include, for example, polymerizable groups that can undergo electrophilic, nucleophilic, or free radical reaction, derivatives with such groups being useful to form polymers comprising polymeric chains having a plurality of pendant perfluoroalkyl groups. Such derivatives include carboxylic and sulfonic acids and their metal and ammonium salts; esters, including alkyl and alkenyl esters; amides; alcohols; acrylates and methacrylates (and polyacrylates and polymethacrylates); mercaptans or thiols; alkenyl ethers; and the like.

Thus, Z can comprise such moieties as —COOH, —COOM$_{1/v}$, —COONH$_4$, —CH$_2$COOR, —CONR$^1$R$^2$, —NR$^1$R$^2$, —CONR$^1$R$^3$A, —OH, —OSO$_3$M$_{1/v}$, —SO$_3$M$_{1/v}$, —SO$_3$NH$_4$, —SO$_2$NR$^1$R$^2$, —SO$_2$NR$^1$R$^3$A, —SO$_3$R, —SH, —CN, —CH$_2$NR$^1$R$^2$, —CH$_2$OCOCR$^4$=CH$_2$, —CH=CH$_2$, and the like, where M is a metal atom having a valence "v", such as a monovalent metal atom like K or Na; R is alkyl (for example, having from 1 to about 14 carbon atoms), aryl (for example, having from about 6 to about 10 or 12 ring carbon atoms), or a combination thereof (for example, alkaryl or aralkyl); R$^1$ and R$^2$ are each independently H or R; R$^3$ is alkylene (for example, having from 1 to about 13 carbon atoms); R$^4$ is H or CH$_3$; A is an aliphatic or aromatic moiety, which optionally can contain a carboxyl or sulfonic acid group or an alkali metal or ammonium salt or ester thereof, a carboxamido group, a sulfonamido group, or can contain 1 to 3 hydroxyl groups, 1 or more ether-oxygen or oxirane-oxygen atoms, a cyano group, or one or more primary, secondary, or tertiary amino groups, or a quaternized amino group, or other functional group. Preferably, Z is selected from hydroxyl, amino, carboxyl, mercapto, sulfonato, and vinyl moieties, and combinations thereof.

For example, the polymethylene halide telomers of the invention can be further converted to the corresponding polymethylene alcohols. For such conversion, the above-described preparation process preferably further comprises (a) combining at least one polymethylene halide telomer with at least one metal carboxylate (preferably, sodium acetate); and (b) subjecting the resulting polymethylene carboxylate to alkanolysis (preferably, methanolysis or ethanolysis); wherein the combining and the subjecting are carried out under substantially anhydrous conditions.

The above-described derivatives can be converted to other derivative fluorochemical compositions. For example, hydroxyl group-containing derivatives (the corresponding polymethylene alcohols) can be converted to corresponding sulfate derivatives useful as surfactants as described, for example, in U.S. Pat. No. 2,803,656 (Ahlbrecht et al.) or phosphate derivatives useful as textile and leather treating agents as described, for example, in U.S. Pat. No. 3,094,547 (Heine). Hydroxyl group-containing derivatives can also be reacted with isocyanates to make carbamoyl-containing derivatives such as urethanes, carbodiimides, biurets, allophanates, and guanidines useful in treating fibrous substrates such as textiles as described, for example, in U.S. Pat. No. 3,398,182 (Guenthner et al.), U.S. Pat. No. 4,024,178 (Landucci), U.S. Pat. No. 4,668,406 (Chang), U.S. Pat. No. 4,606,737 (Stern), and U.S. Pat. No. 4,540,497 (Chang et al.), respectively.

Amine functional derivatives can be converted to corresponding amine salts useful as surfactants, as described, for example, in U.S. Pat. No. 2,764,602 (Ahlbrecht) and U.S. Pat. No. 2,759,019 (Brown et al.) or amphoteric surfactants as described, for example, in U.S. Pat. No. 4,484,990 (Bultman et al.). Amine functional derivatives can be successively reacted to form amphoteric surfactants as described, for example, in U.S. Pat. No. 4,359,096 (Berger) (see Table I thereof).

The polymerizable functional derivatives (for example, where Z is acrylate, methacrylate, or urethane, or a combination (for example, urethane acrylate) thereof) can be used to make polymers such as polyacrylates, polymethacrylates, polyesters, polyurethanes, polyamides, and polyvinyl ethers. Such polymers can be made by conventional step-growth, chain-growth, or graft polymerization techniques or processes. Step-growth polymers can be made, for example, from those derivatives having hydroxyl, carboxyl, isocyanato, or amino polymerizable groups. The acrylate, methacrylate, or vinyl derivatives can be used to make chain-growth polymers, such as polyacrylates.

Fluorochemical ethylenically unsaturated derivatives can be homopolymerized to make homopolymers, or can be copolymerized with copolymerizable monomers to make random, alternating, block, and graft polymers. Useful copolymerizable monomers include fluorine-containing and fluorine-free (or hydrocarbon) monomers (for example, methyl methacrylate, ethyl acrylate, butyl acrylate, octadecylmethacrylate, acrylate and methacrylate esters of poly(oxyalkylene) polyol oligomers and polymers such as poly(oxyethylene) glycol dimethacrylate, glycidyl methacrylate, ethylene, vinyl acetate, vinyl chloride, vinylidene chloride, vinylidene fluoride, acrylonitrile, vinyl chloroacetate, isoprene, chloroprene, styrene, butadiene, vinylpyridine, vinyl alkyl ethers, vinyl alkyl ketones, acrylic and methacrylic acid, 2-hydroxyethyl acrylate, N-methylolacrylamide, 2-(N,N,N-trimethylammonium)ethyl methacrylate, and the like, and mixtures thereof).

The resulting polymers can be applied in the form of an aqueous or non-aqueous solution or emulsion as a coating or finish to modify the free surface energy of a substrate, (for example, a non-porous substrate such as plastic and ceramic or a fibrous or porous substrate such as textile (for example, nylon carpet fiber or polyester outerwear fabrics), leather, paper, paperboard, and wood) to impart oil and water repellency thereto, using conventional application techniques (for example, spraying or dipping).

The relative amounts of various comonomers that can be used with the polymerizable derivatives generally can be selected empirically and can depend on the substrate to be treated, the properties desired from the fluorochemical treatment (for example, the degree of oil and/or water repellency desired), and the mode of application to the substrate. Generally, in the case of copolymers, of the interpolymerized or repeating units in the polymer chain, from about 5 to about 95 mole percent of such units can contain pendant perfluoroalkyl groups. The resulting fluoropolymers can be blended with other or known polymers, such as perfluoromethyl-terminated fluoroaliphatic vinyl polymers, and the blend can be used to modify surface properties (for example, of textiles such as fabrics) to provide them with improved properties such as oil and water repellency.

Derivatives that are useful as surfactants generally can have a polar group such as $-CO_2Na$, $-SO_2NHC_3H_6N^+(CH_3)_3 Cl^-$, $-SO_2N(C_2H_5)(C_2H_4O)_8H$, and $-CONHC_3H_6N^+ (CH_3)_2CH_2CO_2^-$, and the like, these moieties being representative of the polar groups in anionic, cationic, non-ionic, and amphoteric surfactants, respectively. The surfactants can be useful in improving or imparting properties to aqueous and non-aqueous (organic) liquid systems such as wetting, penetration, spreading, leveling, foaming, foam stabilization, flow properties, emulsification, dispersability, and oil, water, and soil repellency. The liquid system generally can comprise a liquid phase (in which the surfactant will be dissolved or dispersed) and one or more other phases selected from the group consisting of another liquid phase, a gas phase, and a phase of dispersed solids (for example, polymer solids), and the system can be in the form of an emulsion, suspension, or foam (such as an air foam). Examples of such liquid systems or application areas for such surfactants, include rinsing, cleaning, etching, and plating baths, floor polish emulsions, photographic processes, water base coatings, powder coatings, solvent based coatings, alkaline cleaners, fluoropolymer emulsions, soldering systems, and specialty inks, such as described, for example, in 3M Bulletin 98-0211-2213-4 (38.3) BPH.

The derivatives useful as surfactants also can be incorporated into or mixed with other substances. For example, if sufficiently thermally stable, they can be incorporated into polymeric materials (for example, polyamides such as nylon, or polyolefins such as polypropylene) that are cast, blown, extruded, or otherwise formed into shaped articles, such as films and fibers, the so-incorporated derivatives modifying the properties of the shaped articles, such as the oil and water repellency of their surfaces. The surfactants can also be mixed with other surfactants, such as hydrocarbon surfactants and/or conventional fluorochemical surfactants (for example, those disclosed in U.S. Pat. Nos. 2,567,011 and 2,732,398), and such mixed surfactants can be used to form, for example, aqueous, film-forming foams as described in U.S. Pat. No. 3,562,156 (Francen).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc., in the examples and the rest of the specification are by weight, unless noted otherwise. Solvents and other reagents used were obtained from Aldrich Chemical Company, St. Louis, Mo., unless otherwise noted.

Test Methods

Nuclear Magnetic Resonance (NMR)
$^1$H and $^{19}$F NMR spectra were run on a Varian UNITY plus 400 Fourier transform NMR spectrometer (available from Varian NMR Instruments, Palo Alto, Calif.).

Gas Chromatography/Mass Spectroscopy (GCMS)
GCMS samples were run on, for example, a Finnigan TSQ7000 mass spectrometer (available from Thermo Electron Corporation, Waltham, Mass.).

Gas Chromatography (GC)
GC samples were run on a Hewlett Packard 6890 Series Gas Chromatograph, obtainable from Agilent Technologies, Palo Alto, Calif.

Dynamic Contact Angle Measurement (DCA)
Contact angle measurements were made on sample coatings using as-received reagent-grade hexadecane (obtained from Aldrich, St. Louis, Mo.) and de-ionized water filtered through a filtration system (obtained from Millipore Corporation, Billerica, Mass.), on a video contact angle analyzer (commercially available as product number VCA-2500XE from AST Products, Billerica, Mass.). Reported values are the averages of five measurements.

Differential Scanning Calorimetry (DSC)
DSC samples were run on a Differential Scanning Calorimeter (Elmer 7 Series Thermal Analysis System).

| Table of Abbreviations | |
|---|---|
| Abbreviation or Trade Designation | Description |
| m.p. | Melting point, measured at ambient pressure unless otherwise specified |
| b.p. | Boiling point, measured at ambient pressure unless otherwise specified |

Table of Abbreviations

| Abbreviation or Trade Designation | Description |
|---|---|
| Wt. or wt. | Weight, measured in grams or in percent (%) as specified |
| g or g. | Gram or grams |
| $M_n$ | Number average molecular weight |

Materials

Ethylene was obtained from Oxygen Service Company, St. Paul, Minn.

t-Butyl benzoylperoxide was obtained from Sigma-Aldrich Chemical Company, St. Louis, Mo.

n-$C_4F_9I$ was obtained from TCI America, Portland, Oreg., and is available from Sigma-Aldrich Chemical Company, St. Louis, Mo.

$C_4F_9SO_7F$ was obtained from 3M Company, St. Paul, Minn.

$C_6F_{13}I$ is available from Sigma-Aldrich Chemical Company, St. Louis, Mo.

$(CF_3)_2CFCH_2CH_2I$ can be prepared by adding $(CF_2)_2CFI$ to ethylene at 60° C. with 2,2'-azo-bis(isobutyronitrile) (AIBN), using methods described in U.S. Pat. No. 3,145,222 (Brace).

$CF_3CF_2CH_2I$ can be prepared by reaction of $C_2F_5CH_2OSO_2C_6H_4$-4-$CH_3$ (available from Synquest Labs, Inc. Alachua, Fla.) with NaI, as described below for $CF_3(CF_2)_3SO_2N(Me)CH_2CH_2I$.

$CF_3(CF_2)_3SO_2N(Me)CH_2CH_2I$ was made as follows: $CF_3(CF_2)_3SO_2N(Me)CH_2CH_2OH$ was reacted with an excess of thionyl chloride in methylene chloride at 25-45° C. to give $CF_3(CF_2)_3SO_2N(Me)CH_2CH_2Cl$, which (7.1 g) was mixed with a solution of 6.0 g NaI in acetone. The resulting solution was stirred at reflux, and the conversion to $CF_3(CF_2)_3SO_2N(Me)CH_2CH_2I$ was followed by GC. At 24 hours, conversion was 14 percent, and 6.0 g NaI was added; at 3 days, conversion was 46 percent; at 6 days, conversion was 72 percent, and 6.0 g NaI was added; at 13 days, 96 percent conversion was achieved. The resulting product was precipitated with water and recrystallized from hexane to provide 6.2 g white plates with a m.p. of 80-82° C.

$FO_2S(CF_2)_2O(CF_2)_2I$ was obtained from Sigma-Aldrich Chemical Company, St. Louis, Mo.

$C_3F_6O(isoC_3F_6O)_5CF(CF_3)I$ can be prepared essentially as described by Chen et. al. in J. Fluorine Chem. 65, 59 (1993).

$I(CF_2)_4I$ was obtained from Sigma-Aldrich Chemical Company, St. Louis, Mo.

$CF_3(CF_2)_7Br$ was obtained from 3M Company, St. Paul, Minn., and is available from Sigma-Aldrich Chemical Company, St. Louis, Mo.

Sodium acetate was obtained from Sigma-Aldrich Chemical Company, St. Louis, Mo.

Dimethylsulfoxide (DMSO) was obtained from Alfa Aesar, Ward Hill, Mass.

Tetrahydrofuran (THF) was obtained from EMD Chemicals, Inc., Gibbstown, N.J.

p-Toluenesulfonic acid was obtained from J.T. Baker, Phillipsburg, N.J.

$NaHCO_3$ was obtained from EMD Chemicals, Inc., Gibbstown, N.J.

Dibutyltin dilaurate was obtained from Sigma-Aldrich Chemical Company, St. Louis, Mo.

1,2-Dimethoxyethane was obtained from EMD Chemicals, Inc., Gibbstown, N.J.

$MgSO_4$ was obtained from EMD Chemicals, Inc., Gibbstown, N.J.

2,2'-Azobis(2-methylbutyronitrile) was obtained from El duPont de Nemours & Co., Wilmington, Del., as Vazo™ 67.

Ethyl acetate was obtained from EMD Chemicals, Inc., Gibbstown, N.J.

Methanol was obtained from EMD Chemicals, Inc., Gibbstown, N.J.

$CH_2$=CHCOCl was obtained from Sigma-Aldrich Chemical Company, St. Louis, Mo.

Diisopropylethylamine, (i-$Pr_2NEt$) was obtained from EMD Chemicals, Inc., Gibbstown, N.J.

Octadecylacrylate (ODA) was obtained from San Esters Corp., Linden, N.J.

Hexamethylene diisocyanate was obtained from Bayer Polymers LLC of Pittsburgh, Pa., as Desmodur™ N3300A.

Example 1

Telomerization of Ethylene using Perfluorobutyl Iodide

A 43 mL stainless steel autoclave was charged with 8 g of $C_4F_9I$ and 0.0202 g of t-butyl benzoylperoxide. After the autoclave was cooled in a dry ice bath and degassed using a vacuum pump, 18 g of ethylene was introduced. The autoclave was shaken and slowly heated to 100° C. and held at 100° C. overnight. The autoclave was then cooled to room temperature, any remaining gases were released, and 10.5 g of a wax-like product was recovered. The wax-like product, comprising a mixture of telomers having the formula [$C_4F_9(CH_2)_nI$], was characterized by using GCMS and GC. GCMS was used to identify the telomers present by molecular weight, and GC was utilized to determine the wt. percent (%) of the telomers present in the product mixture. The GC data showing the wt. % of each telomer [$C_4F_9(CH_2)_nI$] in the product mixture of Example 1 are reported below using the format {retention time in minutes, corresponding n in [$C_4F_9(CH_2)_nI$], wt. % of corresponding telomer [$C_4F_9(CH_2)_nI$] in the mixture} as follows:

5.5 minutes, n=6, 4.4%; 6.8 minutes, n=8, 8.1%; 7.9 minutes, n=10, 10.5%; 8.8 minutes, n=12, 11.6%; 9.8 minutes, n=14, 11.4%; 10.7 minutes, n=16, 10.5%; 11.5 minutes, n=18, 9.4%; 12.3 minutes, n=20, 8.2%; 12.9 minutes, n=22, 6.8%; 13.5 minutes, n=24, 5.3%; 14.1 minutes, n=26, 4.1%; 14.7 minutes, n=28, 3.1%; 15.2 minutes, n=30, 2.5%; 15.8 minutes, n=32, 2.2%; 16.3 minutes, n=34, 2.2%; 17.0 minutes, n=36, 2.5%; 18.0 minutes, n=38, 2.0%; 19.3 minutes, n=40, 1.4%. A chromatogram of the actual GC data showed graphically that the reaction products reached a maximum weight percentage at approximately n=12 to 14, in contrast with previously reported distributions which generally reached a maximum at n=1 to 2 with at least some fluorine-containing telogens.

Conversion of the GC data from wt. % to mole %, followed by summation gave a number average molecular weight of $M_n$=582, corresponding to an number average value of n in the formula $C_4F_9(CH_2)_nI$ of 16.6 for the product mixture of Example 1.

In addition, the product of Example 1 was analyzed using $^1$H-NMR. $^1$H-NMR resonances observed at 1.2 to 2.0 parts per million (ppm) were ascribed to $C_4F_9CH_2(CH_2)_{n-2}$— and those observed at 3.2 ppm were ascribed to a terminal —$CH_2I$. The area under the resonances was measured as 90.41 and 5.45, respectively. The addition of 1 (to account for the $CH_2$ moiety contained in the terminal —$CH_2I$ group) to the ratio of the area for the resonances at 1.2 to 2.0 ppm (90.41) to that of the resonance at 3.2 ppm (5.45) gave an estimated number average value n for the formula [$C_4F_9(CH_2)_nI$] of 17.6.

Thus, the number average n values determined from the GC (16.6) and $^1$H-NMR (17.6) analyses were relatively consistent and significantly higher than the number average n values of 1 to 2 (by GC) of the previously reported distributions using at least some fluorine-containing telogens.

Examples 2-10

Telomerization of Ethylene using Various Different Telogens

Examples 2-10 were carried out in essentially the same manner as that described above for Example 1, except that the type and the amount of the reactants were varied as summarized in Table 1 below. For Example 2, a 183 mL stainless steel autoclave was used.

TABLE 1

| Example No. | Telogen, Weight of Telogen (g) | Weight of Ethylene (g) | Ethylene:Telogen Molar Ratio | Weight of t-Butyl Benzoylperoxide (g) |
|---|---|---|---|---|
| 2 | n-$C_4F_9I$, 8.0 | 18 | 27.8 | 0.202 |
| 3 | n-$C_4F_9I$, 10.6 | 66 | 76.9 | 0.242 |
| 4 | $I(CF_2)_4I$, 2.1 | 20 | 154.4 | 0.0761 |
| 5 | $CF_3(CF_2)_7Br$, 2.3 | 16.1 | 124.2 | 0.00755 |
| 6 | $(CF_3)_2CFCH_2CH_2I$, 8 | 16.2 | 23.4 | 0.196 |
| 7 | $(CF_3)_2CFCH_2CH_2I$, 3.4 | 15 | 50.8 | 0.08 (AIBN) |
| 8 | $CF_3(CF_2)_3SO_2N(Me)$—$CH_2CH_2I$, 2.0 | 16.7 | 139.3 | 0.074 |
| 9 | $FO_2S(CF_2)_2O(CF_2)_2I$, 2.0 | 18.3 | 134.0 | 0.0734 |
| 10 | $C_3F_6O(i-C_3F_6O)_5CF$—$(CF_3)I$, $M_n = 1200$, 2.0 | 16.2 | 346.6 | 0.0704 |

Estimated number average n values for the product telomer mixtures of formula [$R(CH_2)_nX$] were determined for each of Examples 2-10 and are reported in Table 2 below (where R and X correspond to the R and X of a particular telogen, RX, that was used for the particular Example). The estimated number average n values reported in Table 2 were determined and calculated using the $^1$H-NMR technique described above for Example 1.

TABLE 2

| Example No. | Number Average Value of n for $R(CH_2)_nX$ Telomer Distribution |
|---|---|
| 2 | 17.6 |
| 3 | 22.6 |
| 4 | 56.2 |
| 5 | 30.2 |
| 6 | 15.5 |
| 7 | 28.8 |
| 8 | 27.4 |
| 9 | 57.4 |
| 10 | 19.5 |

Example 11

Telomerization of Ethylene using Perfluorobutyl Iodide with Recycle

A 183 mL stainless steel autoclave was charged with 17.2 g of $C_4F_9I$ and 0.457 g of t-butyl perbenzoate. After the autoclave was cooled in a dry ice bath and degassed using a vacuum pump, 14.4 g of ethylene was added. The autoclave was shaken and heated to 100° C. and held at 100° C. overnight. The autoclave was then cooled to room temperature, any remaining gases were released, and 26.0 g of a wax-like product was recovered. The product was analyzed by $^1$H-NMR to be $C_4F_9(CH_2)_{16.6}I$. 10.0 g of this product was placed in the 183 mL stainless steel autoclave together with 0.270 g t-butyl perbenzoate and 66.2 g ethylene. The above-described reaction process was repeated. After holding at 100° C. overnight, the autoclave was cooled to room temperature, any remaining gases were released, and 12.8 g of product was recovered. The number average value of n of the product was determined by $^1$H-NMR to be 23.4.

Example 12

Conversion of a Telomer Distribution to the Corresponding Alcohols, $C_4F_9(CH_2)_{17.6}OH$ A mixture of 8.1 g of $C_4F_9(CH_2)_{17.6}I$ (number average n=17.6), 8.1 g sodium acetate, and 80 mL DMSO was stirred and heated to 135° C. After 18 hours at 135° C., the resulting mixture was poured into water. The resulting solid was collected and re-dissolved in THF. The THF solution was filtered to remove residual salts and then was concentrated to 7 g of wax-like product. GC and $^1$H-NMR confirmed complete conversion to $C_4F_9(CH_2)_{17.6}OC(O)CH_3$. A mixture of 7 g of this ester, 0.19 g p-toluenesulfonic acid, and 500 mL ethanol was charged to a flask and heated at reflux for 48 hours. NaHCO$_3$ (0.19 g) was added, and the resulting solid was removed by filtration. After solvent was removed, 6.5 g of wax-like product remained. GC and $^1$H-NMR confirmed complete conversion to $C_4F_9(CH_2)_{17.6}OH$.

Example 13

Fluoropolymer Preparation and Testing
Preparation of Poly($C_4F_9(CH_2)_{17.6}OC(O)NHCH_2CH_2OC(O)C(Me)$=$CH_2$):

$C_4F_9(CH_2)_{17.6}OH$ (1.0 g, $M_n$=482.3), OCNCH$_2$CH$_2$OC(O)C(Me)=CH$_2$ (0.321 g), dibutyltin dilaurate (2 drops), and 10 mL of 1,2-dimethoxyethane were charged to a flask. The resulting mixture was stirred at room temperature overnight. The stirred mixture was poured into water, and the resulting collected organic layer was washed with water and then dried over MgSO$_4$. After removal of solvent, 1.2 g of white solid remained, which was determined to be $C_4F_9(CH_2)_{17.6}OC(O)NHCH_2CH_2OC(O)C(Me)$=$CH_2$ by $^1$H-NMR.

A solution of 0.518 g of the above-prepared methacrylate monomer and 0.005 g VAZO™ 67 in 1.5 g ethyl acetate was charged to a 5 mL ampoule. After three freeze (−80° C.)-pump (0.001316 atmosphere (1 mm Hg))-thaw cycles, the ampoule was sealed and immersed in a water bath at 60° C.

for 3 days. The resulting solution was poured into methanol, and 0.34 g of solid was collected. A coating of this solid material was formed by dipping a nylon film into a 10-20% by weight ethyl acetate solution of the material, followed by heating the coated nylon film to 120-150° C. DCA analysis of the coated film gave the following values: 116 and 99 degrees respectively for advancing and receding water contact angles, and 65 and 23 degrees respectively for advancing and receding hexadecane contact angles.

Preparation of Poly($C_4F_9(CH_2)_{17.6}OC(O)CH=CH_2$):

$C_4F_9(CH_2)_nOH$ (1.0 g, $M_n=482.3$), 1.88 g of $CH_2=CHCOCl$, 2.67 g of i-$Pr_2NEt$, and 10 mL of 1,2-dimethoxyethane were charged to a flask. The resulting mixture was stirred at room temperature overnight. The mixture was poured into water, and the resulting collected organic layer was washed with water and dried over $MgSO_4$. After removal of solvent, 0.9 g of white product remained, which was analyzed by $^1$H-NMR to be $C_4F_9(CH_2)_{17.6}OC(O)CH=CH_2$, and then 0.3063 g of this acrylate monomer, 0.0044 g VAZO™ 67, and 0.8 g ethyl acetate were charged to a 5 mL ampoule. After three freeze-pump-thaw-cycles (as described above), the ampoule was sealed and immersed in a water bath at 65° C. for 3 days. The resulting solution was poured into methanol, and the resulting solid was collected. DSC showed that the solid had a melting peak around 43° C. A coating of this solid material was formed by dipping a nylon film into a 10-20% by weight ethyl acetate solution of the material, followed by heating the coated nylon film to 120-150° C. DCA analysis of the coated film gave the following values: 122 and 109 degrees respectively for advancing and receding water contact angles, and 72 and 25 degrees respectively for advancing and receding hexadecane contact angles.

0.215 g of the above-prepared acrylate monomer, 0.0922 g of ODA, 0.0056 g of VAZO™ 67, and 0.8 g of ethyl acetate was charged to a 5 mL ampoule. After three thaw-freezing-pump cycles, the ampoule was sealed and immersed in a water bath at 65° C. for 3 days. The resulting solution was poured into methanol, and the resulting solid was collected. DSC of the solid showed a melting peak around 43° C. A coating of this solid material was formed by dipping a nylon film into a 10-20% by weight ethyl acetate solution of the material, followed by heating the coated nylon film to 120-150° C. DCA analysis of the coated film gave the following values: 121 and 102 degrees respectively for advancing and receding water contact angles, and 64 and 26 degrees respectively for advancing and receding hexadecane contact angles.

Preparation of Polyurethane Using Desmodur™ N3300:

$C_4F_9(CH_2)_{17.6}OH$ (0.80 g, $M_n=482.3$) was dissolved in ethyl acetate and heated azeotropically to remove water. 0.323 g Desmodur™ N3300 and 5 drops of dibutyltin dilaurate were added. The resulting mixture was refluxed overnight. Evaporation of solvent gave a solid product. A coating of this solid material was formed by dipping a nylon film into a 10-20% by weight ethyl acetate solution of the material, followed by heating the coated nylon film to 120-150° C. DCA analysis of the coated film gave the following values: 121 and 71 degrees respectively for advancing and receding water contact angles, and 68 and 29 degrees respectively for advancing and receding hexadecane contact angles.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A composition comprising a distribution of telomers of ethylene and at least one fluoroalkyl or perfluoroalkyl halide, said telomers comprising at least one polymethylene segment ($—(CH_2)_n—$) and at least one halomethyl group ($—CXH_2$) and optionally comprising at least one non-fluorine heteroatom, and said halogen being selected from iodine and bromine; wherein said distribution has a number average ratio of the methylene moieties of said polymethylene segment to said halomethyl groups of at least 15.

2. The composition of claim 1, wherein said halogen is iodine.

3. The composition of claim 1, wherein said halogen is bromine.

4. The composition of claim 1, wherein said number average ratio is at least 20.

5. The composition of claim 1, wherein said heteroatom is selected from iodine, bromine, nitrogen, oxygen, sulfur, and mixtures thereof.

6. The composition of claim 1, wherein said distribution is selected from the class of product telomer distributions that is represented by the following general formula:

$$RC(R)(R)—(CH_2)_n—X \qquad (IV)$$

wherein each R is independently hydrogen, fluorine, or an alkyl, fluoroalkyl, or perfluoroalkyl group of 1 to 25 carbon atoms that optionally comprises at least one non-fluorine heteroatom and/or at least one alicyclic moiety, with the proviso that optionally two said R groups are bonded together to form an alicyclic ring having 5 to 7 ring carbon atoms, and with the further proviso that at least one of said R groups comprises fluorine; X is iodine or bromine; and n is a number average value of at least 15.

7. The composition of claim 6, wherein said heteroatom is selected from iodine, bromine, nitrogen, oxygen, sulfur, and mixtures thereof.

8. The composition of claim 6, wherein at least one said R group is hydrogen or fluorine.

9. The composition of claim 6, wherein said n is a number average value of at least 20.

10. The composition of claim 1, wherein said distribution is selected from the class of product telomer distributions that is represented by the following general formula:

$$R''CH(R')—(CH_2)_n—X \qquad (V)$$

wherein R'' is fluorine or a fluoroalkyl or perfluoroalkyl group of 1 to 25 carbon atoms that optionally comprises at least one non-fluorine heteroatom and/or at least one alicyclic moiety; R' is hydrogen, fluorine, or a fluoroalkyl or perfluoroalkyl group of 1 to 25 carbon atoms that optionally comprises at least one non-fluorine heteroatom and/or at least one alicyclic moiety; X is iodine or bromine; with the proviso that optionally R'' and R' are bonded together to form an alicyclic ring having from 5 to 7 ring carbon atoms; and n is a number average value of at least 15.

11. The composition of claim 1, wherein said distribution is selected from the class of product telomer distributions that is represented by the following general formula:

$$R''''CF(R''')—(CH_2)_n—X \qquad (VI)$$

wherein R'''' is a perfluoroalkyl group of 1 to 25 carbon atoms that optionally comprises at least one alicyclic moiety and/or at least one non-fluorine halogen atom; R''' is fluorine or a perfluoroalkyl group of 1 to 25 carbon atoms; X is iodine or bromine; with the proviso that at least one of R'''' and R''' comprises at least one non-halogen heteroatom, and with the further proviso that R'''' and R''' optionally are bonded together to form an alicyclic ring having from 5 to 7 ring carbon atoms; and n is a number average value of at least 15.

12. The composition of claim 1, wherein said distribution is selected from $C_4F_9(CH_2)_nI$, $C_5F_{11}(CH_2)_nBr$, $C_6F_{13}(CH_2)_nI$, $CF_3(CH_2)_nI$, $CF_3CF_2(CH_2)_nI$, $(CF_3)_2NCF_2(CH_2)_nI$, $CF_3C_2F_4(CH_2)_nI$, $C_3F_7O(C_3F_6O)_5CF(CF_3)(CH_2)_nI$, $C_4F_9SO_2N(CH_3)(CH_2)_nI$, $FSO_2C_2F_4OC_2F_4(CH_2)_nI$, $CH_3OC(O)CF_2(CH_2)_nI$, $FOC(O)CF_2(CH_2)_nI$, $(CF_3)_2CF(CH_2)_nI$, $(CF_3)_2N(CH_2)_nI$, $(CF_3)_2CHO(CH_2)_nI$, $SF_5CF_2(CH_2)_nI$, $CF_3OC_2F_4(CH_2)_nBr$, $(CF_3)_2CH(CH_2)_nI$, $(CF_3)_3C(CH_2)_nBr$, $C_4F_9SO_2N(CH_3)CH_2C(O)(CH_2)_nI$, where n is a number average value of at least about 15, and mixtures thereof.

13. A composition comprising a distribution of telomers of ethylene and at least one fluoroalkyl or perfluoroalkyl halide, said telomers comprising at least one polymethylene segment (—$(CH_2)_n$—) and at least one halomethyl group (—$CXH_2$) and optionally comprising at least one non-fluorine heteroatom, and said halogen being selected from iodine and bromine; wherein said distribution has a number average ratio of the methylene moieties of said polymethylene segment to said halomethyl groups of at least 15; and wherein said halogen is replaced with an organic functional moiety, Z, that is selected from carbonyl-containing, sulfur-containing, alkenyl-containing, nitrogen-containing, and oxygen-containing moieties, and combinations thereof.

14. The composition of claim 13, wherein said Z is selected from acrylate, methacrylate, and urethane moieties, and combinations thereof.

15. A composition comprising a distribution of telomers of ethylene and at least one fluoroalkyl or perfluoroalkyl halide, said distribution being selected from the class of product telomer distributions that is represented by the following general formula:

$$RC(R)(R)-(CH_2)_n-X \qquad (IV)$$

wherein each R is independently hydrogen, fluorine, or an alkyl, fluoroalkyl, or perfluoroalkyl group of 1 to 6 carbon atoms that optionally comprises at least one non-fluorine heteroatom, or a perfluoroalkyl group of 1 to 25 carbon atoms that comprises at least one oxygen atom, with the proviso that at least one of said R groups comprises fluorine; X is iodine or bromine; and n is a number average value of at least 15.

16. The composition of claim 15, wherein said n is a number average value of at least 20.

17. A fluoropolymer prepared by polymerization off a composition comprising a distribution of telomers of ethylene and at least one fluoroalkyl or perfluoroalkyl halide, said telomers comprising at least one polymethylene segment (—$(CH_2)_n$—) and at least one halomethyl group (—$CXH_2$) and optionally comprising at least one non-fluorine heteroatom, and said halogen being selected from iodine and bromine; wherein said distribution has a number average ratio of the methylene moieties of said polymethylene segment to said halomethyl groups of at least 15; and wherein said halogen is replaced with an organic functional moiety, Z, that is selected from acrylate, methacrylate, and urethane moieties, and combinations thereof.

18. A coating composition comprising the fluoropolymer of claim 17 and a liquid carrier.

19. A process comprising applying the coating composition of claim 18 to at least a portion of at least one surface of at least one substrate.

20. A coated article comprising at least one substrate bearing the coating composition of claim 18 or the fluoropolymer of claim 17 on at least a portion of at least one surface thereof.

* * * * *

UNITED STATES PATENT AND TRADEMARK OFFICE
CERTIFICATE OF CORRECTION

PATENT NO. : 8,236,425 B2
APPLICATION NO. : 12/519573
DATED : August 7, 2012
INVENTOR(S) : George G Moore et al.

It is certified that error appears in the above-identified patent and that said Letters Patent is hereby corrected as shown below:

In the Specifications:

Column 9,
Line 7, delete "$C_3F_7O(C_3F_6O)_5CF(CF)(CH_2)_nI,$" and insert --$C_3F_7O(C_3F_6O)_5CF(CF_3)(CH_2)_nI$,--, therefor.

Column 13,
Line 22, delete "$C_4F_9SO_7F$" and insert --$C_4F_9SO_2F$--, therefor.

In the Claims:

Column 20,
Line 16, Claim 17, delete "off" and insert --of--, therefor.

Signed and Sealed this
Twenty-third Day of April, 2013

Teresa Stanek Rea
*Acting Director of the United States Patent and Trademark Office*